United States Patent [19]

Hendrickx et al.

[11] Patent Number: 5,872,131
[45] Date of Patent: Feb. 16, 1999

[54] PHENYL-OXO-ALKYL-(4-PIPERIDINYL) BENZOATE DERIVATIVES

[75] Inventors: Marie-Louise Hendrickx, Turnhout; Kurt Godfried Cornelius Emile Van Daele, Borgerhout; Peter Jules Victor Van Daele, Grimbergen; Glenn Kurt Ludo Van Daele, Turnhout; Jean-Paul René Marie André Bosmans, Edegem; Marc Gustaaf Celine Verdonck, Gierle, all of Belgium

[73] Assignee: Janssen Pharmaceutica, N.V., Beerse, Belgium

[21] Appl. No.: 809,502

[22] PCT Filed: Sep. 19, 1995

[86] PCT No.: PCT/EP95/03690

§ 371 Date: Mar. 24, 1997

§ 102(e) Date: Mar. 24, 1997

[87] PCT Pub. No.: WO96/10026

PCT Pub. Date: Apr. 4, 1996

[30] Foreign Application Priority Data

Sep. 27, 1994  [EP]  European Pat. Off. ............ 94.202.791

[51] Int. Cl.$^6$ .................. A61K 31/445; C07P 211/44
[52] U.S. Cl. .................. 514/320; 514/327; 546/196; 546/218
[58] Field of Search .................. 546/196, 218; 514/320, 327

[56] References Cited

U.S. PATENT DOCUMENTS

| | | | |
|---|---|---|---|
| 4,853,394 | 8/1989 | King | 514/329 |
| 5,130,312 | 7/1992 | Van Daele | 514/252 |
| 5,262,418 | 11/1993 | Van Daele | 514/258 |
| 5,374,637 | 12/1994 | Van Daele | 514/320 |

FOREIGN PATENT DOCUMENTS

| | | |
|---|---|---|
| 0 309 043 | 3/1989 | European Pat. Off. . |
| 0 389 037 | 9/1990 | European Pat. Off. . |
| 0 389 037 A1 | 9/1990 | European Pat. Off. . |
| 0 445 862 | 9/1991 | European Pat. Off. . |
| 0 445 862 A2 | 9/1991 | European Pat. Off. . |
| 3810552 | 10/1989 | Germany . |
| 93/03725 | 3/1993 | WIPO . |
| WO 93/03725 | 3/1993 | WIPO . |
| 94/08995 | 4/1994 | WIPO . |
| WO 94/08995 | 4/1994 | WIPO . |

OTHER PUBLICATIONS

Ohshiko et al. "Effect of Y–25130 on gastrointestinal . . . " Japan. J. Phar. v.61 suppl. 195p (p–61) 1993.
Stedman's "Medical Dictionary" Williams and Wilkins p. 533 1995.
Ohshiko, "Effect of Y–25130 on Gastrointestinal. . .", Japanese Journal of Pharmacology, vol 61, supplement I, pp. 61, 1993.
Stedman, Stedman's Medical Dictionary, pp. 533, 1995.

*Primary Examiner*—John Kight
*Assistant Examiner*—D. Margaret M. Mach
*Attorney, Agent, or Firm*—Ellen Ciambrone Coletti

[57] ABSTRACT

The present invention is concerned with novel benzoate derivatives having the formula

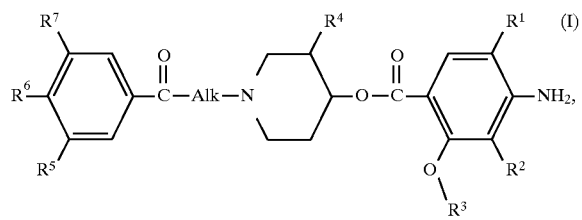

the N-oxide forms, the pharmaceutically acceptable acid addition salts and the stereochemically isomeric forms thereof, wherein $R^1$ is halo or $C_{1-6}$alkylsulfonylamino; either $R^2$ is hydrogen and $R^3$ is $C_{1-6}$alkyl, $C_{2-6}$alkenyl or $C_{2-6}$alkynyl; or $R^2$ and $R^3$ taken together form a bivalent radical of formula —CH=CH— (a), —(CH$_2$)$_2$— (b), or —(CH$_2$)$_3$— (c); in the bivalent radicals of formula (a), (b) or (c) one or two hydrogen atoms may be replaced by $C_{1-6}$alkyl; Alk is $C_{1-6}$alkanediyl; $R^4$ is hydrogen or $C_{1-6}$alkyloxy; $R^5$, $R^6$ and $R^7$ each independently are hydrogen, halo, $C_{1-6}$alkyl, $C_{1-6}$alkyloxy; or $R^5$ and $R^6$ taken together may also form a bivalent radical of formula: —NR$^8$C(O)NR$^9$—, —NH—C(NHR$^{10}$)=N—, —O—(CH$_2$)$_m$—O—; $R^8$ and $R^9$ each independently are hydrogen or $C_{1-6}$alkyl; $R^{10}$ is hydrogen, $C_{1-6}$alkylcarbonyl, $C_{1-6}$alkyloxycarbonyl; m is 1 or 2. Pharmaceutical compositions comprising said compounds, processes for preparing compounds and compositions as well as the use as a medicine, in particular for the treatment of intestinal disorders involving a decreased colon motility are described.

16 Claims, No Drawings

PHENYL-OXO-ALKYL-(4-PIPERIDINYL) BENZOATE DERIVATIVES

CROSS-REFERENCE TO RELATED APPLICATIONS

This application is the national stage of application No. PCT/EP 95/03690, filed on Sep. 19, 1995, which application claims priority from EP 94.202.791.3, filed on Sep. 27, 1994.

The present invention is concerned with novel benzoate derivatives, pharmaceutical compositions comprising said novel compounds, processes for preparing compounds and compositions, and the use thereof as a medicine, in particular in the treatment of conditions involving a decreased motility of the colon.

In our EP-0,389,037-A, published on Sep. 26, 1990, N-(3-hydroxy-4-piperidinyl) (dihydrobenzofuran or dihydro-2H-benzopyran)carboxamide derivatives are disclosed as having gastrointestinal motility stimulating properties. In our EP-0,445,862-A, published on Sep. 11, 1991, N-(4-piperidinyl) (dihydrobenzofuran or dihydro-2H-benzopyran)carboxamide derivatives are disclosed also having gastrointestinal motility stimulating properties. WO 93/03725 (SmithKline Beecham), published on Mar. 4, 1993, generically discloses the use as $5HT_4$ receptor antagonists of esters of general formula X—CO—Y—Z, wherein X can be a substituted phenyl, Y can be oxygen, and Z can be a substituted piperidine moiety. WO 94/08995 (SmithKline Beecham), published on Apr. 28, 1994 generically discloses, for instance, substituted 7-benzofuran carboxylates also having $5HT_4$ antagonistic activity. The latter two patent applications describe the use of the $5HT_4$ antagonistic compounds in the treatment of irritable bowel syndrome (IBS), in particular the diarrhoea aspects of IBS.

Unexpectedly, we have discovered that the present novel compounds show intestinal prokinetic activity. Hence, the presently disclosed compounds show utility in treatment of conditions involving a decreased motility of the intestine, especially the colon.

The present invention is concerned with novel benzoate derivatives having the formula

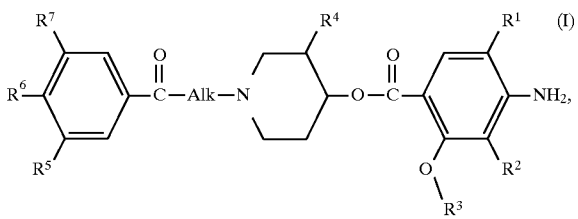

the N-oxide forms, the pharmaceutically acceptable acid addition salts and the stereochemically isomeric forms thereof, wherein:

$R^1$ is halo or $C_{1-6}$alkylsulfonylamino;

either $R^2$ is hydrogen and $R^3$ is $C_{1-6}$alkyl, $C_{2-6}$alkenyl or $C_{2-6}$alkynyl; or $R^2$ and $R^3$ taken together form a bivalent radical of formula:

—CH=CH— (a),

—(CH$_2$)$_2$— (b), or

—(CH$_2$)$_3$— (c);

in the bivalent radicals of formula (a), (b) or (c) one or two hydrogen atoms may be replaced by $C_{1-6}$alkyl;

Alk is $C_{1-6}$alkanediyl;

$R^4$ is hydrogen or $C_{1-6}$alkyloxy;

$R^5$, $R^6$ and $R^7$ each independently are hydrogen, halo, $C_{1-6}$alkyl, $C_{1-6}$alkyloxy;

or $R^5$ and $R^6$ taken together may also form a bivalent radical of formula:

$R^8$ and $R^9$ each independently are hydrogen or $C_{1-6}$alkyl;

$R^{10}$ is hydrogen, $C_{1-6}$alkylcarbonyl, $C_{1-6}$alkyloxycarbonyl; and m is 1 or 2.

As used in the foregoing definitions and hereinafter, halo is generic to fluoro, chloro, bromo and iodo; $C_{1-6}$alkyl defines straight and branched chain saturated hydrocarbon radicals having from 1 to 6 carbon atoms such as, for example, methyl, ethyl, propyl, butyl, pentyl, hexyl, 1-methylethyl, 2-methylpropyl and the like; $C_{2-6}$alkenyl defines straight and branched chain hydrocarbon radicals containing one double bond and having from 2 to 6 carbon atoms such as, for example, ethenyl, 2-propenyl, 3-butenyl, 2-butenyl, 2-pentenyl, 3-pentenyl, 3-methyl-2-butenyl, 3-hexenyl, and the like; $C_{2-6}$alkynyl defines straight and branched chain hydrocarbon radicals containing one triple bond and having from 2 to 6 carbon atoms such as, for example, ethynyl, 2-propynyl, 3-butynyl, 2-butynyl, 2-pentynyl, 3-pentynyl, 3-hexynyl and the like; $C_{1-6}$-alkanediyl defines bivalent straight or branched chain hydrocarbon radicals containing from 1 to 6 carbon atoms such as, for example, methylene, 1,2-ethanediyl, 1,3-propanediyl, 1,4-butanediyl, 1,5-pentanediyl, 1,6-hexanediyl.

The pharmaceutically acceptable acid addition salts as mentioned hereinabove are meant to comprise the therapeutically active non-toxic acid addition salt forms which the compounds of formula (I) are able to form. The latter can conveniently be obtained by treating the base form with such appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic, maleic, fumaric, malic, tartaric, citric, methanesulfonic, ethanesulfonic, benzenesulfonic, p-toluenesulfonic, cyclamic, salicylic, p-aminosalicylic, pamoic and the like acids. The term addition salt as used hereinabove also comprises the solvates which the compounds of formula (I) as well as the salts thereof, are able to form. Such solvates are for example hydrates, alcoholates and the like. Conversely the salt form can be converted by treatment with alkali into the free base form.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration and $C_{2-6}$alkenyl radicals may have the E- or Z-configuration. Stereochemically isomeric forms of the compounds of formula (I) are obviously intended to be embraced within the scope of this invention.

Some of the compounds of formula (I) may also exist in their tautomeric form. Such forms although not explicitly indicated in the above formula are intended to be included within the scope of the present invention. For instance, compounds of formula (I) wherein $R^5$ and $R^6$ are taken together to form a bivalent radical of formula (d) wherein $R^8$, $R^9$ or both are hydrogen may exist in their corresponding tautomeric form.

The N-oxide forms of the compounds of formula (I) are meant to comprise those compounds of formula (I) wherein one or several nitrogen atoms are oxidized to the so-called N-oxide, particularly those N-oxides wherein the piperidine-nitrogen is N-oxidized.

$R^1$ suitably is fluoro, chloro or bromo, preferably $R^1$ is chloro; $R^3$, when not taken together with $R^2$, suitably is $C_{1-6}$alkyl, preferably methyl; when $R^2$ and $R^3$ are taken together a bivalent radical of formula (b) is preferred; Alk is suitably 1,2-ethanediyl, 1,3-propanediyl, or 1,4-butanediyl, preferably 1,3-propanediyl; $R^4$ is suitably hydrogen or methoxy; $R^5$, $R^6$ and $R^7$ are suitably hydrogen, $C_{1-6}$alkyl, $C_{1-6}$alkyloxy or chloro, preferably methyl, methoxy or hydrogen; or when $R^5$ and $R^6$ are taken together a bivalent radical of formula (d) or (e) is preferred, especially a radical of formula (d).

Interesting compounds of formula (I) are those compounds of formula (I) wherein $R^1$ is chloro.

Further interesting compounds of formula (I) are those compounds of formula (I) wherein $R^2$ and $R^3$ taken together form a bivalent radical of formula (b).

More interesting compounds are those interesting compounds wherein Alk is 1,3-propanediyl.

Preferred compounds are those more interesting compounds wherein $R^5$, $R^6$ and $R^7$ are methoxy.

Also preferred compounds are those more interesting compounds wherein $R^7$ is hydrogen and $R^5$ and $R^6$ are taken together to form a radical of formula (d) wherein $R^8$ and $R^9$ are hydrogen.

Other preferred compounds are those more interesting compounds wherein $R^5$ and $R^7$ are methyl and $R^6$ is methoxy.

Most preferred compounds are:
cis-3-methoxy-1-[4-oxo-4-(3,4,5-trimethoxyphenyl)butyl]-4-piperidinyl 4-amino-5-chloro-2,3-dihydro-7-benzofurancarboxylate;
1-[4-oxo-4-(3,4,5-trimethoxyphenyl)butyl]-4-piperidinyl 4-amino-5-chloro-2,3-dihydro-7-benzofurancarboxylate;
1-[4-(2,3-dihydro-2-oxo-1H-benzimidazol-5-yl)-4-oxobutyl]-4-piperidinyl 4-amino-5-chloro-2,3-dihydro-7-benzofurancarboxylate; and
1-[4-(4-methoxy-3,5-dimethylphenyl)-4-oxobutyl]-4-piperidinyl 4-amino-5-chloro-2,3-dihydro-7-benzofurancarboxylate;
the stereoisomeric forms thereof and the pharmaceutically acceptable acid addition salts thereof.

In order to simplify the structural representations of the compounds of formula (I) and certain intermediates thereof, the radical of formula

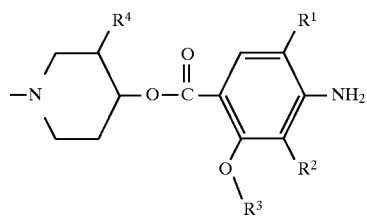

will hereafter be represented by the symbol D and the radical

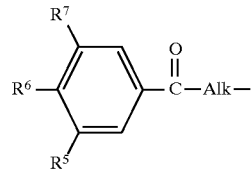

will hereafter be represented by L.

In the following preparations, the reaction products may be isolated from the reaction mixture and, if necessary, further purified according to methodologies generally known in the art such as, for example, extraction, distillation, crystallization, trituration and chromatography.

The compounds of formula (I) may be prepared by N-alkylating a piperidine of formula (II) with an intermediate of formula (III).

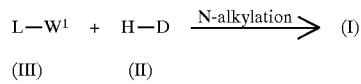

$W^1$ in the intermediate of formula (III) is an appropriate leaving group such as, for example, halo, e.g. chloro, bromo or iodo, or a sulfonyloxy group, e.g. methanesulfonyloxy, toluenesulfonyloxy and the like leaving groups. The N-alkylation reaction of (II) with (III) is conveniently conducted following art-known alkylation procedures.

The compounds of formula (I) may also be prepared by the esterification of an alcohol of formula (IV) wherein $R^4$ and L are as defined hereinabove, with a carboxylic acid of formula (V) wherein $R^1$, $R^2$ and $R^3$ are as defined hereinabove, or a functional derivative thereof, such as an acylhalide, a symmetrical or mixed anhydride or an ester, preferably an activated ester, following art-known procedures.

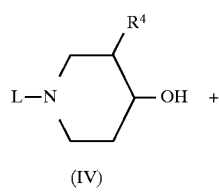

-continued

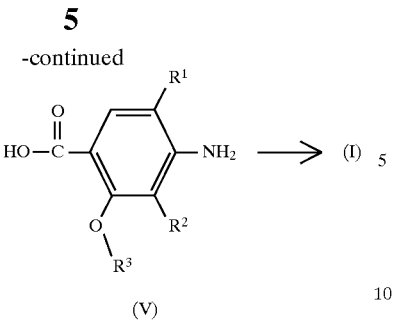

(V)

It may be expedient to protect the amino group of the intermediate of formula (V) during the course of the reaction to avoid undesired side reactions. Said amino protecting group is removed after completion of the esterification. Suitable protecting groups comprise readily removable groups such as $C_{1-4}$alkylcarbonyl, $C_{1-4}$alkyloxycarbonyl, phenylmethyl and the like protective groups.

Compounds of formula (I) wherein $R^5$ and $R^6$ are taken together and form a radical of formula (d), said compounds being represented by formula (I-d), may be prepared by reacting an intermediate of formula (VI) with 1,1'-carbonylbis-1H-imidazole or a functional derivative thereof, following art-known reaction procedures.

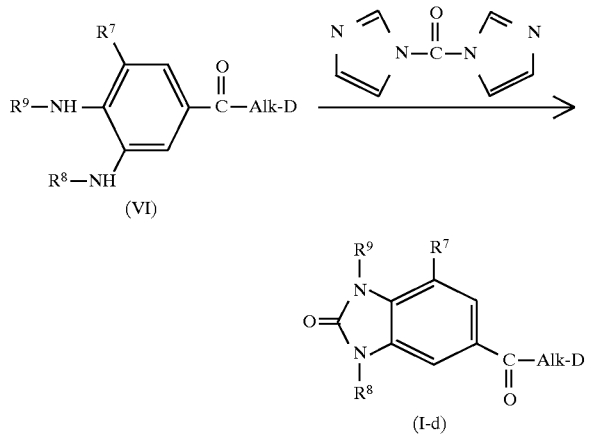

Compounds of formula (I) wherein $R^5$ and $R^6$ are taken together and form a radical of formula (e), said compounds being represented by formula (I-e), may be prepared by reacting an intermediate of formula (VI) wherein $R^8$ and $R^9$ are both hydrogen, said intermediates being represented by formula (VI-a), with an intermediate of formula (VII), following art-known reaction procedures.

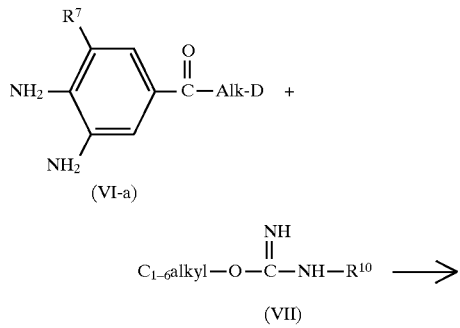

-continued

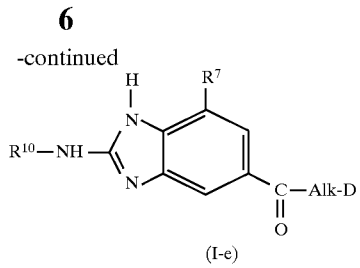

(I-e)

The compounds of formula (I) may also be converted into each other. For instance, the compounds of formula (I), wherein $R^{10}$ is hydrogen may be converted into compounds of formula (I), wherein $R^{10}$ is $C_{1-6}$alkylcarbonyl or $C_{1-6}$alkyloxycarbonyl, by art-known N-acylation reactions.

The compounds of formula (I) wherein $R^3$ is $C_{2-6}$alkenyl or $C_{2-6}$alkynyl may be converted into compounds of formula (I) wherein $R^3$ is the corresponding saturated alkylradical by art-known hydrogenation techniques.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The intermediates of formula (II) may be derived from an appropriately substituted piperidine of formula (VIII) with an intermediate acid of formula (V) or a functional derivative thereof, following art-known ester forming procedures, and subsequently removing the protective group P, following art-known procedures. P represents a readily removable protective group such as $C_{1-4}$alkylcarbonyl, $C_{1-4}$alkyloxycarbonyl, phenylmethyl and the like protective groups.

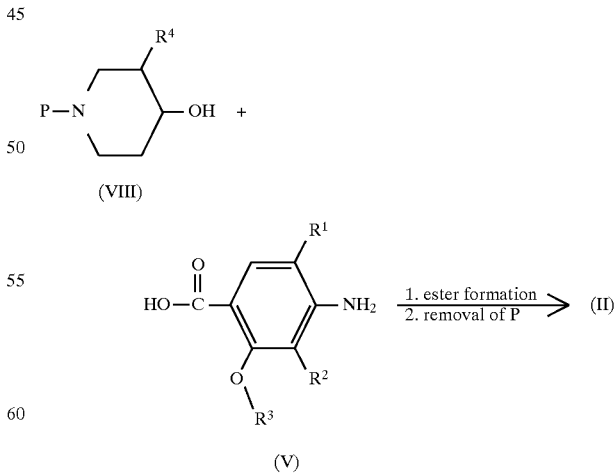

The preparation of intermediate acids of formula (V) is disclosed in EP-0,389,037-A.

The intermediates of formula (VI-a) may be prepared by reduction of an intermediate of formula (IX) with a suitable reducing agent such as, for example, a combination of platinum on activated carbon and hydrogen, in a reaction-inert solvent such as, for example, tetrahydrofuran.

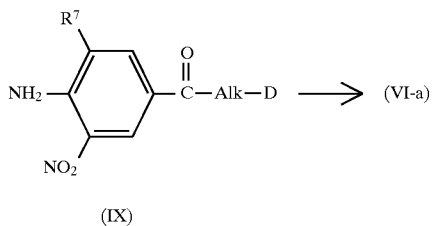

(IX)

Said intermediates of formula (IX) may be prepared by N-alkylating a piperidine of formula (II) with an intermediate of formula (X) wherein $W^1$ is an appropriate leaving group, such as, for example, a halogen atom, in an analogous way as the compounds of formula (I) are prepared from intermediates (II) and (III).

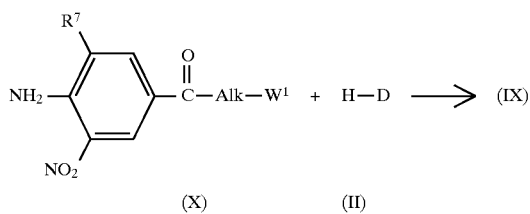

(X)      (II)

The intermediates of formula (VIII'), wherein $P^1$ represents P as defined hereinabove as well as hydrogen, may be prepared by reduction of an intermediate of formula (XI) following art-known methods. In particular, the intermediates of formula (VIII'), wherein $R^4$ is $C_{1-6}$alkyloxy, said intermediates being represented by formula (VIII'-a), and wherein $R^4$ and the hydroxyl group have a cis-configuration may be prepared by reduction of an intermediate of formula (XI-a) using a reductive agent such as substituted borohydrides, e.g. lithium tris-sec-butylborohydride, potassium tris-sec-butylborohydride, substituted aluminiumhydrides, lithium-tri-tert-butoxyaluminohydride and the like, in a reaction-inert solvent such as, for example, tetrahydrofuran. It may be advantageous to perform the reaction at a lower temperature, preferably at a temperature below −70° C. Using stereochemically pure reagents said reduction may be performed in a stereospecific manner.

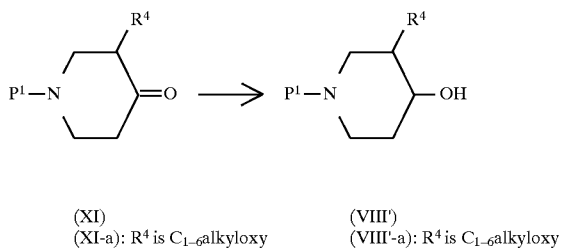

(XI)      (VIII')
(XI-a): $R^4$ is $C_{1-6}$alkyloxy      (VIII'-a): $R^4$ is $C_{1-6}$alkyloxy The cis and trans diastereomeric racemates of the compounds of formula (I), or any of the other intermediates may also be resolved into their optical isomers, cis(+), cis(−), trans(+) and trans(−) by the application of art-known methodologies. Diastereoisomers may be separated by physical separation methods such as selective crystallization and chromatographic techniques, e.g. counter current distribution, and enantiomers may be separated from each other by the selective crystallization of their diastereomeric salts with enantiomerically pure acids or their enantiomerically pure derivatives.

The compounds of formula (I) and the intermediates of formula (II) and (VI), the N-oxide forms, the pharmaceutically acceptable salts and stereoisomeric forms thereof possess favourable intestinal motility stimulating properties. In particular the present compounds show significant motility enhancing effects on the small and large intestine. The latter properties are evidenced by the results obtained in the "Guinea Pig Ileum Coaxial Stimulation" test and the "Colon motility in conscious dog" test. Both said test are described hereinafter. Some of the compounds also show activity in the "Lidamidine test in dogs".

In view of their useful intestinal motility enhancing properties the subject compounds may be formulated into various forms for administration purposes.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I), (II) or (VI) due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In view of their capability to stimulate the motility of the intestinal system and in particular their capacity to enhance the motility of the colon, the subject compounds are useful to normalize or to improve the intestinal transit in subjects suffering from symptoms related to disturbed motility, e.g. a decreased peristalsis of the small and large intestine alone or in combination with delayed gastric emptying. In view of the utility of the compounds of the present invention, there is provided a method of treating warm-blooded animals suffering from motility disorders of the intestinal system such as, for example, constipation, pseudo-obstruction, intestinal atony, post-operative intestinal atony, irritable bowel syndrome (IBS), drug-induced delayed transit, and in particular impaired colonic transit. Said method comprises the systemic administration of an effective intestinal stimulating amount of a compound of formula (I), a N-oxide, a pharmaceutically acceptable acid addition salt or a possible stereoisomeric form thereof, to warm-blooded animals. Hence, the use of a compound of formula (I) as a medicine is provided, and in particular the use of a compound of formula (I) for the manufacture of a medicine for treating conditions involving a decreased motility of the colon.

In general it is contemplated that a therapeutically effective amount would be from about 0.001 mg/kg to about 10 mg/kg body weight, preferably from about 0.02 mg/kg to about 5 mg/kg body weight. A method of treatment may also include administering the active ingredient on a regimen of between two or four intakes per day.

EXPERIMENTAL PART

A. Preparation of Intermediates

Example 1 a) Sodium borohydride (7.7 g) was added portionwise to a stirred solution of 3-methoxy-1-(phenylmethyl)-4-piperidinone (44.8 g) in ethanol (610 ml). Upon completion, the whole was cooled to room temperature and stirring was continued for 3 hours at room temperature. The reaction mixture was concentrated to a volume of about 150 ml. Water (300 ml) was added to the concentrate and all traces of ethanol were evaporated. After cooling, the mixture was extracted with diethylether. The extract was washed with water, dried, filtered and evaporated. The oily residue was purified by column-chromatography over silica gel (eluent: $CHCl_3/CH_3OH$ 96/4). The pure fractions were collected and the eluent was evaporated. The residue was separated by column-chromatography over silica gel (eluent: hexane/$CHCl_3/(CH_3OH/NH_3)$ 50/50/1). The first fraction was collected and the eluent evaporated, yielding 11.5 g (25.5%) of trans-3-methoxy-1-(phenylmethyl)-4-piperidinol (intermediate 1). The second fraction was collected and the eluent evaporated, yielding 7.7 g (17.1%) of cis-3-methoxy-1-(phenylmethyl)-4-piperidinol (intermediate 2).

a') A solution of 3-methoxy-1-(phenylmethyl)-4-piperidinone (4.4 g) in tetrahydrofuran was cooled to −75° C. Lithium tris-sec-butylborohydride was added dropwise and the reaction mixture was stirred for 2 hours at −70° C. Acetic acid 10% (100 ml) was added dropwise at room temperature. The organic solvent was evaporated. The aqueous residue was alkalized with $NH_4OH$, then extracted twice with diisopropylether. The separated organic layer was washed with water, dried over $MgSO_4$, filtered and the solvent was evaporated. The residue was purified by short column chromatography over silica gel (eluent: $CH_2Cl_2/CH_3OH$ 95/5 upgrading to 98/2), yielding 1.3 g (29.4%) of cis-3-methoxy-1-(phenylmethyl)-4-piperidinol (intermediate 2).

b) A mixture of 11.5 g of intermediate (2) and 150 ml of methanol was hydrogenated at normal pressure and at room temperature with 2 g of palladium-on-charcoal catalyst (10%). After the calculated amount of hydrogen was taken up, the catalyst was filtered off and the filtrate was evaporated. The residue was purified by column-chromatography over silica gel (eluent: $CHCl_3/(CH_3OH/NH_3)$ 85/15). The pure fractions were collected and the eluent was evaporated, yielding 3.6 g (53%) of cis-3-methoxy-4-piperidinol as an oily residue (intermediate 3).

c) A solution of bis(1,1'-dimethylethyl)dicarbonate (65.5 g) in $CHCl_3$ (100 ml) was added dropwise to a solution of intermediate (3) (34 g) in trichloromethane (350 ml) and the reaction mixture was stirred for 3 hours at room temperature. The reaction mixture was washed with water and ammonia, then with water. The separated organic layer was dried over $MgSO_4$, filtered and the solvent was evaporated. The residue (79 g) was purified by column chromatography over silica gel (eluent: $CH_2Cl_2/(CH_3OH/NH_3)$ 97/3, upgrading to 95/5). The pure fractions were collected and the solvent was evaporated, yielding 58 g of (±)-1,1-dimethylethyl cis-4-hydroxy-3-methoxy-1-piperidinecarboxylate (96.4% crude residue) (intermediate 4).

d) Sodium hydride (4 g) was added to a solution of intermediate (4) (19.4 g) in tetrahydrofuran (400 ml). The mixture was stirred and refluxed for 3 hours (solution I). 1,1'-carbonylbis-1H-imidazole (13.6 g) was added to a suspension of 4-amino-5-chloro-2,3-dihydro-7-benzofurancarboxylic acid (18 g) in acetonitrile (400 ml) and this mixture was stirred for 2 hours at room temperature. The solvent was evaporated. The residue was dissolved in tetrahydrofuran (400 ml), giving solution II. At room temperature, solution (II) was poured out into solution (I) and the reaction mixture was stirred for 2 hours at room temperature. The solvent was evaporated. The residue was partitioned between $CH_2Cl_2$ and $H_2O$. The organic layer was separated and the aqueous layer was extracted twice with $CH_2Cl_2$. The separated organic layer was dried over $MgSO_4$, filtered and the solvent was evaporated. The residue was purified by short column chromatography over silica gel (eluent: $CH_2Cl_2/CH_3OH$ 98/2). The desired fractions were collected and the solvent was evaporated, yielding 32 g (±)-cis-1-[(1,1-dimethylethoxy)carbonyl]-3-methoxy-4-piperidinyl 4-amino-5-chloro-2,3-dihydro-7-benzofurancarboxylate (87%) (intermediate 5).

e) A mixture of intermediate (5) (32 g) in tetrahydrofuran (500 ml) and hydrochloric acid (50 ml) was stirred and refluxed for 30 minutes. The reaction mixture was cooled and alkalized with $NH_4OH$. The layers were separated. The aqueous layer was extracted with tetrahydrofuran. The separated organic layer was evaporated. The residue was purified by column chromatography over silica gel (eluent: $CH_2Cl_2/(CH_3OH/NH_3)$ 93/7). The pure fractions were collected and the solvent was evaporated. The residue was crystallized from acetonitrile. The precipitate was filtered off and dried (vacuum; 80 ° C.), yielding 6.4 g of (±)-cis-3-methoxy-4-piperidinyl 4-amino-5-chloro-2,3-dihydro-7-benzofurancarboxylate (26%) (intermediate 6).

Example 2 a) A mixture of 4-amino-5-chloro-2,3-dihydro-7-benzofurancarboxylic acid (4.3 g) in thionyl chloride (100 ml) and $CHCl_3$ (200 ml) was stirred and refluxed for 2 hours. The mixture was cooled and the solvent was evaporated. Toluene was added and evaporated again, yielding 4.8 g of 4-amino-5-chloro-2,3-dihydro-7-benzofurancarbonyl chloride (100% crude residue) (intermediate 7).

b) A solution of 1,1-dimethylethyl 4-hydroxy-1-piperidinecarboxylate (4.02 g) and N,N-dimethyl-4- pyridinamine (3.7 g) in dichloromethane (200 ml) was stirred at room temperature. A solution of intermediate (7) (4.8 g) in $CH_2Cl_2$ (200 ml) was poured into the solution. The reaction mixture was stirred for 3 hours at room temperature. The mixture was washed with water, a 5% NaOH solution and again water. The organic layer was separated, dried over $MgSO_4$, filtered and the solvent was evaporated. The residue (7.4 g) was purified by column chromatography over silica gel (eluent: $CH_2Cl_2/CH_3OH$ 98/2). The pure fractions were collected and the solvent was evaporated, yielding 4.7 g of 1,1-dimethylethyl 4-[[(4-amino-5-chloro-2,3-dihydro-7-benzofuranyl)carbonyl]oxy]-1-piperidinecarboxylate (59%) (intermediate 8).

c) A mixture of intermediate (8) (7 g) in tetrahydrofuran (20 ml) and hydrochloric acid (20 ml) was stirred and refluxed for 2 hours. The reaction mixture was cooled and alkalized with $NH_4OH$. The organic layer was removed by decantation and the solvent was evaporated. The residue was purified by column chromatography over silica gel (eluent: $CH_2Cl_2/(CH_3OH/NH_3)$ 92/8). The pure fractions were collected and the solvent was evaporated. The residue (5.5 g) was repurified by high-performance liquid chromatography (column: 200 g Kromasil; 10 μm; 100 Å; eluent: (0.5% $NH_4OAc$ in water)/methanol 70/30). The pure fractions were collected and extracted with $NH_3/CH_2Cl_2$. The extract was evaporated. The residue was crystallized from acetonitrile. The precipitate was filtered off and dried (vacuum; 70° C.), yielding 2.60 g of 4-piperidinyl 4-amino-5-chloro-2,3-dihydro-7-benzofurancarboxylate (54%) (intermediate 9).

Example 3 a) A mixture of cyclopropyl (4-amino-3-nitrophenyl) methanone (80 g), prepared as described in U.S. Pat. No. 3,657,267, and concentrated HCl (420 ml) was stirred and refluxed for 30 minutes. The reaction mixture was cooled and water was added. The precipitate was filtered off, washed with water and dried, yielding 80 g (84.5%) of 1-(4-amino-3-nitrophenyl)-4-chloro-1-butanone; mp. 150° C. (intermediate 10).

b) A mixture of intermediate (9) (14.8 g), intermediate (10) (12.13 g) and N,N-diethylethanamine (8.3 ml) in N,N-dimethylformamide (150 ml) was stirred for 20 hours at ±70° C. The solvent was evaporated. The residue was diluted with water and this mixture was extracted twice with $CH_2Cl_2$. The separated organic layer was washed with water, dried over $MgSO_4$, filtered and the solvent evaporated. The residue was purified by column chromatography over silica gel (eluent: $CH_2Cl_2/CH_3OH$ 90/10). The desired fractions were collected and the solvent was evaporated. The residue (10 g) was crystallized from diisopropylether. The precipitate was filtered off and dried, yielding 8.3 g (33%) of 1-[4-(4-amino-3-nitrophenyl)-4-oxobutyl]-4-piperidinyl 4-amino-5-chloro-2,3-dihydro-7-benzofurancarboxylate (intermediate 11).

c) A mixture of intermediate (11) (8.2 g) in tetrahydrofuran (150 ml) was hydrogenated with platinum on activated carbon (5%) (2 g) as a catalyst. After uptake of $H_2$ (3 equiv), the catalyst was filtered off over dicalite and the filtrate was evaporated. The residue was diluted with water and this mixture was extracted twice with $CH_2Cl_2$. The separated organic layer was washed with water, dried over $MgSO_4$, filtered and the solvent evaporated. The residue (8 g) was purified by column chromatography over silica gel (eluent: $CH_2Cl_2/(CH_3OH/NH_3)$ 92/8). The pure fractions were collected and the solvent was evaporated. The residue (7.5 g) was crystallized from $CH_3CN$. The precipitate was filtered off and dried, yielding 5.43 g (70.5%) of 1-[4-(3,4-diaminophenyl)-4-oxobutyl]-4-piperidinyl 4-amino-5-chloro-2,3-dihydro-7-benzofurancarboxylate; mp. 173.4° C. (intermediate 12).

B. Preparation of Final Compounds

Example 4

A mixture of intermediate (6) (2.3 g), 4-chloro-1-(3,4,5-trimethoxyphenyl)-1-butanone (2 g), sodium carbonate (2.1 g) and potassium iodide (catalytic quantity) in 4-methyl-2-pentanone (150 ml; previously dried over $MgSO_4$) was stirred and refluxed overnight. The reaction mixture was cooled, washed with water, dried over $MgSO_4$, filtered and the filtrate was evaporated. The residue was purified by column chromatography over silica gel (eluent: $CH_2Cl_2$, upgrading to $CH_2Cl_2/(CH_3OH/NH_3)$ 97/3). The pure fractions were collected and the solvent was evaporated. The residue was dissolved in methanol and converted into the ethanedioic acid salt with ethanedioic acid (0.6 g). The mixture was boiled, then cooled and the precipitate was filtered off and recrystallized from 2-propanol. The precipitate was dissolved in aqueous $NH_4OH/CH_2Cl_2$. The organic layer was separated, dried over $MgSO_4$, filtered and the solvent was evaporated. The residue was stirred in boiling diisopropylether, cooled and the resulting precipitate was filtered off and dried (vacuum; 80° C.), yielding 1.10 g of (±)-cis-3-methoxy-1-[4-oxo- 4-(3,4,5-trimethoxyphenyl) butyl]-4-piperidinyl 4-amino-5-chloro-2,3-dihydro-7-benzofurancarboxylate (28%); mp. 132.3° C. (compound 1). In a similar manner there were also prepared:

1-[4-oxo-4-(3,4,5-trimethoxyphenyl)butyl]-4-piperidinyl 4-amino-5-chloro-2,3-dihydro-7-benzofurancarboxylate ethanedioate(1:1); mp. 177.8° C. (compound 2);

1-[4-(4-ethylphenyl)-4-oxobutyl]-4-piperidinyl 4-amino-5-chloro-2,3-dihydro-7-benzofurancarboxylate; mp. 121.3° C. (compound 3);

1-[4-(3,5-dichlorophenyl)-4-oxobutyl]-4-piperidinyl 4-amino-5-chloro-2,3-dihydrobenzofurancarboxylate; mp. 122.6° C. (compound 4);

1-[4-(3,4-dimethoxyphenyl)-4-oxobutyl]-4-piperidinyl 4-amino-5-chloro-2,3-dihydro-7-benzofurancarboxylate; mp. 156.3° C. (compound 5);

1-[4-(4-methoxyphenyl)-4-oxobutyl]-4-piperidinyl 4-amino-5-chloro-2,3-dihydro-7-benzofurancarboxylate; mp. 136.4° C. (compound 6);

1-[4-(4-methoxy-3,5-dimethylphenyl)-4-oxobutyl]-4-piperidinyl 4-amino-5-chloro-2,3-dihydro-7-benzofurancarboxylate (E)-2-butenedioate(1:1); mp. 171.2° C. (compound 7).

Example 5

4-(4-hydroxy-1-piperidinyl)-1-(3,4,5-trimethoxyphenyl)-1-butanone (3.3 g) was added to a solution of sodium hydride (0.4 g) in tetrahydrofuran (100 ml) (solution I) under a $N_2$ flow. A mixture of 5-amino-6-chloro-3,4-dihydro-2H-1-benzopyran-8-carboxylic acid (2.14 g) and 1,1'-carbonylbis-1H-imidazole (2 g) in acetonitril (100 ml) was stirred for 2 hours at room temperature and the solvent was evaporated. The residue was dissolved in tetrahydrofuran (100 ml) (solution II). At room temperature, solution (II) was poured out into solution (I) and the reaction mixture was stirred for 4 hours at room temperature. The solvent was evaporated. The residue was diluted with water and extracted twice with $CH_2Cl_2$. The separated organic layer was washed with water, dried over $MgSO_4$, filtered and the solvent was evaporated. The residue was purified by column chromatography over silica gel (eluent: $CH_2Cl_2$/hexane/$(CH_3OH/NH_3)$ 50/42/3). The desired fractions were collected and the solvent was evaporated. The residue (2.3 g) was purified by high-performance liquid chromatography over silica gel (eluent: $CH_2Cl_2/CH_3OH$ 90/10). The pure fractions were collected and the solvent was evaporated. The residue (1.2 g) was crystallized from diisopropyl ether. The precipitate was filtered off and dried, yielding 0.93 g of 1-[4-oxo-4-(3,4,5-trimethoxyphenyl)butyl]-4-piperidinyl 5-amino-6-chloro-3,4-dihydro-2H-benzopyran-8-carboxylate (17%); mp. 112.7° C. (compound 8).

In a similar manner there were also prepared:

1-[4-oxo-4-(3,4,5-trimethoxyphenyl)butyl]-4-piperidinyl 4-amino-5-chloro-2,3-dihydro-2,2-dimethyl-7-benzofurancarboxylate; mp. 154.2° C. (compound 9);

1-[4-oxo-4-(3,4,5-trimethoxyphenyl)butyl]-4-piperidinyl 4-amino-5-chloro-2-methoxybenzoate monohydrate; mp. 90° C. (compound 10);

1-[4-oxo-4-(3,4,5-trimethoxyphenyl)butyl]-4-piperidinyl 4-amino-5-chloro-2-methyl-7-benzofurancarboxylate; mp. 128.6° C. (compound 11).

Example 6

A mixture of intermediate (12) (2.4 g) and hydrochloric acid (a few drops) in water (50 ml) was stirred at room temperature. A solution of potassium isocyanate (2.5 g) in water (50 ml) was added and the resulting reaction mixture was stirred and refluxed for 2 hours. The reaction mixture was cooled, alkalized with $NH_4OH$, and then extracted twice with $CH_2Cl_2$. The separated organic layer was dried over $MgSO_4$, filtered, and the solvent evaporated. The residue (2.5 g) was mixed with 1,1'-carbonylbis-1H-imidazole (0.93 g) in tetrahydrofuran (80 ml). The reaction mixture was stirred and refluxed for 2 hours. The solvent was evaporated. The residue was diluted with water and this mixture was extracted twice with $CH_2Cl_2$. The separated organic layer was washed with water, dried over $MgSO_4$, filtered and the solvent evaporated. The residue was crystallized from 2-propanol/methanol. The precipitate was filtered off and dried, yielding 0.53 g of 1-[4-(2,3-dihydro-2-oxo-1H-benzimidazol-5-yl)-4-oxobutyl]-4-piperidinyl 4-amino-5-chloro-2,3-dihydro-7-benzofurancarboxylate (21.2%); mp. 272.7° C. (compound 12).

Example 7

A mixture of intermediate (12) (1.8 g), methyl (α-imino-α-methoxymethyl)carbamate (0.5 g) and acetic acid (0.75 ml) in $CHCl_3$ (100 ml) was stirred and refluxed for 2 days. The reaction mixture was alkalized with $NH_4OH$. The organic layer was separated and the aqueous layer was extracted with $CH_2Cl_2$. The combined organic layers were washed with water, dried over $MgSO_4$, filtered and the solvent evaporated. The residue was crystallized twice from methanol. The precipitate was filtered off and dried, yielding 0.4 g of 1-[4-[2-[(methoxycarbonyl)amino]-1H-benzimidazol-5-yl]-4-oxobutyl]-4-piperidinyl 4-amino-5-chloro-2,3-dihydro-7-benzofurancarboxylate monohydrate (18.7%); mp. 201.6° C. (compound 13).

C. Pharmacological Example

Example 8: Guinea Pig Ileum Coaxial Stimulation

Dunkin Hartley guinea-pigs of both sexes (body weight ±500 g) were killed by decapitation. The ileum was removed and cleansed with warmed and oxygenated Krebs-Henseleit solution. Non-terminal, intact ileum segments, 4.5 cm long, of the guinea pig were vertically suspended with a preload of 1 g in 100 ml Krebs-Henseleit solution (37.5° C.), gassed with a mixture of 95% $O_2$ and 5% $CO_2$. Transmural excitation was applied over the whole length of the ileum segment by means of two platinum electrodes, the anode threaded through the lumen of the ileum, the cathode in the bathing solution. The preparation was excited with single rectangular stimili [1 msec; 0.1 Hz; submaximal response (current leading to 80% of maximal reponse)] from a programmable stimulator. Contractions were measured isometrically. During the stabilization period of 30 min, the strips were repeatedly stretched to a tension of 2 g, in order to obtain a steady state tension of 1 g. Before starting the electrical stimulation, a cumulative dose response curve of acetylcholine was given. The electrical stimulation was started at supramaximal current to determine the maximal amplitude of the twitch responses. When these responses were stable, a submaximal stimulation to obtain 80% of the maximal responses was given until the twitch responses were constant for at least 15 min, whereafter a single dose of the test compound was added to the bath fluid. The amplitude of the twitch response five minutes after the administration of the test compound is compared with the amplitude before the administration of the test compound. The compounds 1, 2, 7 and 13 showed an increase of the amplitude of the twitch response of more than 5% at a concentration of $3.10^{-9}M$.

Example 9: Motility of the Colon in the Conscious Dog

Female beagle dogs, weighing 7–17 kg, were implanted with isometric force transducers, under general anaesthesia and aseptic conditions. To study the colonic motility, transducers were sutured on the colon at 8, 16, 24 and 32 cm distance from the ileocaecal-valve. Dogs were allowed a recovery period of at least two weeks. Experiments were started after a fasting period of ±20 hours, during which water was available ad libitum. During the experiments, dogs were free to move in their cages, using a telemetric (wireless) system. The cages were built in a special room, provided with glass pervious to light in one direction, i.e. the observator could see the dogs while the dogs could not see the observator. Via this system it was possible to observe the dogs for behavioral changes and to determine defecation events. The information from the transducers was transmitted in digitized form by a small, specially built transmitter box. This box was placed in a jacket worn by the dog. The signals were received via a microphone above each cage and were transmitted to a central computer system. One of the parameters in this test is the defecation of the dogs. During the first three hours after administration of the test compound, the dogs were observed to determine whether and when defecation occurred. Compounds 1, 2, 5, 6, 12 and 13 induced defecation in at least 50% of the test animals at doses of 0.31 mg/kg during those first three hours.

D. Composition Examples

The following formulations exemplify typical pharmaceutical compositions in dosage unit form suitable for systemic or topical administration to warm-blooded animals in accordance with the present invention. "Active ingredient" (A.I.) as used throughout these examples relates to a compound of formula (I), a N-oxide form, a pharmaceutically acceptable acid addition salt or a stereochemically isomeric form thereof.

Example 10: Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 of sorbitol 70% solution are added thereto. 40 g of sodium saccharin are dissolved in 0.5 of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example 11: Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example 12: Film-coated Tablets

Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10.000 tablets, each comprising 10 mg of the active ingredient.

Coating

To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concen-trated colour suspension and the whole is homogenated. The tablet cores are coated with the thus obtained mixture in a coating apparatus.

Example 13: Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration (U.S.P. XVII p. 811) and filled in sterile containers.

Example 14: Suppositories 3 g A.I. was dissolved in a solution of 3 g 2,3-dihydroxybutanedioic acid in 25 ml polyethylene glycol 400. 12 G surfactant and triglycerides q.s. ad 300 g were molten together. The latter mixture was mixed well with the former solution. The thus obtained mixture was poured into moulds at a temperature of 37°~38° C. to form 100 suppositories each containing 30 mg of the active ingredient.

We claim:

1. A compound of formula (I)

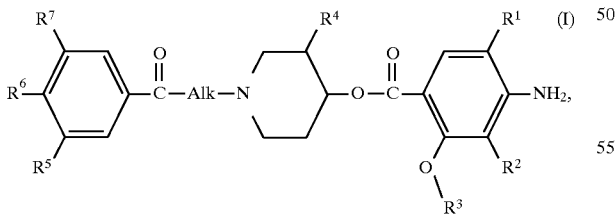

a N-oxide form, a pharmaceutically acceptable acid addition salt or a stereochemically isomeric form thereof, wherein:

$R^1$ is halo or $C_{1-6}$alkylsulfonylamino;

either $R^2$ is hydrogen and $R^3$ is $C_{1-6}$alkyl, $C_{2-6}$alkenyl or $C_{2-6}$alkynyl; or $R^2$ and $R^3$ taken together form a bivalent radical of formula:

—CH=CH—  (a),

—(CH$_2$)$_2$—  (b), or

—(CH$_2$)$_3$—  (c);

in the bivalent radicals of formula (a), (b) or (c) one or two hydrogen atoms may be replaced by $C_{1-6}$alkyl;

Alk is $C_{1-6}$alkanediyl;

$R^4$ is hydrogen or $C_{1-6}$alkyloxy;

$R^5$, $R^6$ and $R^7$ each independently are hydrogen, halo, $C_{1-6}$alkyl, $C_{1-6}$alkyloxy;

or $R^5$ and $R^6$ taken together may also form a bivalent radical of formula:

$R^8$ and $R^9$ each independently are hydrogen or $C_{1-6}$alkyl;

$R^{10}$ is hydrogen, $C_{1-6}$alkylcarbonyl, $C_{1-6}$alkyloxycarbonyl;

m is 1 or 2.

2. A compound as claimed in claim 1 wherein $R^1$ is chloro.

3. A compound as claimed in claim 1 wherein $R^2$ and $R^3$ taken together form a bivalent radical of formula (b).

4. A compound as claimed in claim 1 wherein Alk is 1,3-propanediyl.

5. A compound as claimed in claim 1 wherein the compound is cis-3-methoxy-1-[4-oxo-4-(3,4,5-trimethoxyphenyl) butyl]-4-piperidinyl 4-amino-5-chloro-2,3-dihydro-7-benzofurancarboxylate;

1-[4-oxo-4-(3,4,5-trimethoxyphenyl)butyl]-4-piperidinyl-4-amino-5-chloro-2,3-dihydro-7-benzofurancarboxylate;

1-[4(2,3-dihydro-2-oxo-1H-benzimidazol-5-yl)-4-oxobutyl]-4-piperidinyl 4-amino-5-chloro-2,3-dihydro-7-benzofurancarboxylate;

1-[4-(4-methoxy-3,5-dimethylphenyl)-4-oxobutyl]-4-piperidinyl 4-amino-5-chloro-2,3-dihydro-7-benzofurancarboxylate;

a stereoisomeric form thereof or a pharmaceutically acceptable acid addition salt thereof.

6. A pharmaceutical composition comprising a therapeutically effective amount of a compound as claimed in claim 1 and a pharmaceutically acceptable carrier.

7. An intermediate of formula

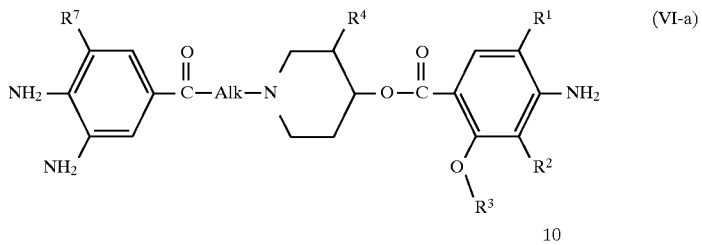

(VI-a)

a N-oxide form, a pharmaceutically acceptable acid addition salt or a stereochemically isomeric form thereof, wherein $R^1$ to $R^4$, $R^7$ and Alk are defined as in claim 1.

8. A method for stimulating intestinal motility in warm-blooded mammals which comprises administering to warm-blooded mammals a therapeutically effective amount of a compound as defined in claim 1.

9. A method for stimulating intestinal motility in warm-blooded mammals which comprises administering to warm-blooded mammals a therapeutically effective amount of a compound as defined in claim 2.

10. A method for stimulating intestinal motility in warm-blooded mammals which comprises administering to warm-blooded mammals a therapeutically effective amount of a compound as defined in claim 3.

11. A method for stimulating intestinal motility in warm-blooded mammals which comprises administering to warm-blooded mammals a therapeutically effective amount of a compound as defined in claim 4.

12. A method for stimulating intestinal motility in warm-blooded mammals which comprises administering to warm-blooded mammals a therapeutically effective amount of a compound as defined in claim 5.

13. A compound as claimed in claim 1, wherein $R^1$ is fluoro, chloro or bromo; $R^3$ is $C_{1-6}$ alkyl or $R^2$ and $R^3$ taken together are a bivalent radical of formula (b); Alk is 1,2 ethanediyl, 1,3-propanediyl or 1,4 butanediyl; $R^4$ is hydrogen or methoxy; $R^5$, $R^6$ and $R^7$ are hydrogen, $C_{1-6}$ alkyl, $C_{1-6}$ alkyloxy or $R^5$ and $R^6$ taken together are a bivalent radical of formula (d) or (e).

14. A compound according to claim 1, wherein $R^5$, $R^6$ and $R^7$ are methoxy.

15. A compound according to claim 1, wherein $R^7$ is hydrogen and $R^5$ and $R^6$ taken together form a radical of formula (d) wherein $R^8$ and $R^9$ are hydrogen.

16. A compound according to claim 1, wherein $R^5$ and $R^7$ are methyl and $R^6$ is methoxy.

* * * * *